United States Patent [19]

McEwan

[11] Patent Number: 5,682,164

[45] Date of Patent: Oct. 28, 1997

[54] PULSE HOMODYNE FIELD DISTURBANCE SENSOR

[75] Inventor: Thomas E. McEwan, Livermore, Calif.

[73] Assignee: The Regents of the University of California, Oakland, Calif.

[21] Appl. No.: 654,407

[22] Filed: May 28, 1996

Related U.S. Application Data

[63] Continuation-in-part of Ser. No. 300,769, Sep. 6, 1994, Pat. No. 5,521,600.

[51] Int. Cl.⁶ .................................................... G01S 13/56
[52] U.S. Cl. ............................. 342/27; 342/22; 342/68; 342/28
[58] Field of Search ............................... 342/22, 27, 28, 342/68

[56] References Cited

U.S. PATENT DOCUMENTS

| | | | |
|---|---|---|---|
| 3,745,578 | 7/1973 | Barrett et al. | 342/201 |
| 3,925,774 | 12/1975 | Amlung | 340/258 |
| 4,213,122 | 7/1980 | Rotman et al. | 340/552 |
| 4,429,302 | 1/1984 | Vandebult | 340/572 |
| 4,439,766 | 3/1984 | Kobayashi et al. | 342/200 |
| 4,553,135 | 11/1985 | Grynberg et al. | 340/564 |
| 4,686,517 | 8/1987 | Fockens | 340/572 |
| 4,891,649 | 1/1990 | Labaar et al. | 342/203 |
| 5,150,123 | 9/1992 | Orlowski et al. | 342/28 |

Primary Examiner—John B. Sotomayor
Attorney, Agent, or Firm—Henry P. Sartorio

[57] ABSTRACT

A field disturbance sensor operates with relatively low power, provides an adjustable operating range, is not hypersensitive at close range, allows co-location of multiple sensors, and is inexpensive to manufacture. The sensor includes a transmitter that transmits a sequence of transmitted bursts of electromagnetic energy. The transmitter frequency is modulated at an intermediate frequency. The sequence of bursts has a burst repetition rate, and each burst has a burst width and comprises a number of cycles at a transmitter frequency. The sensor includes a receiver which receives electromagnetic energy at the transmitter frequency, and includes a mixer which mixes a transmitted burst with reflections of the same transmitted burst to produce an intermediate frequency signal. Circuitry, responsive to the intermediate frequency signal indicates disturbances in the sensor field. Because the mixer mixes the transmitted burst with reflections of the transmitted burst, the burst width defines the sensor range. The burst repetition rate is randomly or pseudo-randomly modulated so that bursts in the sequence of bursts have a phase which varies. A second range-defining mode transmits two radio frequency bursts, where the time spacing between the bursts defines the maximum range divided by two.

20 Claims, 9 Drawing Sheets

| RF | 2.0 GHz | 6.5 GHz |
|---|---|---|
| $R_H$ | 22K | 33K |
| Q | BFR90 | NE68519 |
| $C_R$ | .25p | 0 |
| L | 1 ½" | ½" |
| D | IN5711 | .15P METELLICS |
| $C_W$ | 33p | 51p |

PULSE HOMODYNE FIELD DISTURBANCE SENSOR

RELATED APPLICATIONS

This application is a continuation-in-part (CIP) of Ser. No. 08/300,769 filed Sep. 6, 1994 now U.S. Pat. No. 5,521,600.

The United States Government has rights in this invention pursuant to Contract Number W-7405-ENG-48 between the United States Department of Energy and the University of California for the operation of Lawrence Livermore National Laboratory.

BACKGROUND OF THE INVENTION

1. Field of the Invention

The present invention relates to the field of proximity sensors; and more particularly to field disturbance sensor technology.

2. Description of Related Art

Field disturbance sensors provide a class of motion detectors which have a wide range of applications, such as automotive burglar alarms, house intrusion safety and robotic sensors, industrial counting and process control, automatic door openers, and automotive obstacle detection.

These sensors operate basically by transmitting an electromagnetic signal, and detecting reflected energy in a sensor field. The reflected energy in the sensor field will reach a steady state, when there is no motion within the field. If an object which absorbs or reflects the electromagnetic energy enters the field, then changes in the reflected energy are detected. Field disturbance sensors operating at microwave frequencies are essentially identical to continuous wave (CW) Doppler microwave sensors.

Existing designs suffer several significant problems which limit their application. In particular, they are subject to false alarms caused by interference from other transmitters close to the field of the sensor, or caused by oversensitivity of this type of sensor at close range.

The field disturbance sensors of the prior art rely on relatively high power microwave energy in most applications. These high power microwave applications are limited by communication regulations to a relatively narrow band, which is quite crowded. For instance, the existing field disturbance sensors often operate in the same frequency band as microwave ovens and other high power microwave devices. This subjects the sensors to false readings caused by external transmitters in the range of the receiver on the sensor. Because the allocated frequency range for such uses is relatively narrow, the number of channels which can be used for these purposes is limited. Thus, the number of sensors which may be used in a given field is limited.

Field disturbance sensors of the prior art are also hypersensitive at close range. Thus, a sensor which is tuned to detect motion of a person at about 10 feet, will emit a false alarm when an insect lands on the surface of the antenna. This problem arises because the sensitivity of the device falls off as function of $1/R^2$, where R is the distance from the transmitter to the reflecting object. Also, this hypersensitivity subjects the sensors to false alarms from vibrations or other mechanical disturbances to the sensor.

Accordingly, it is desirable to provide a field disturbance sensor which overcomes the false alarm problems of prior art designs. Also, it is desirable to provide a system which allows multiple sensors to be placed in a single field without interference.

SUMMARY OF THE INVENTION

The present invention provides an improved field disturbance sensor which operates with relatively low power, provides an adjustable operating range, is not hypersensitive at close range, allows co-location of multiple sensors, and is inexpensive to manufacture.

The present invention can be characterized as a sensor which includes a transmitter that transmits a sequence of transmitted bursts of electromagnetic energy. The sequence of bursts has a burst repetition rate, and each burst has a burst width and comprises a number of cycles at a transmitter frequency. The sensor includes a receiver which receives electromagnetic energy at the transmitter frequency. The receiver includes a mixer which mixes a transmitted burst with reflections of the same transmitted burst to produce an intermediate frequency signal. The intermediate frequency is produced by modulating the transmitter frequency or amplitude at the intermediate frequency. Circuitry, coupled to the receiver and responsive to the intermediate frequency signal indicates disturbances in the sensor field. Because the mixer mixes the transmitted burst with reflections of the transmitted burst, the burst width defines the sensor range R, to be about ½ of a burst width.

According to another aspect of the invention, burst rate modulation circuitry is coupled with the transmitter for modulating the burst repetition rate. In one aspect, the burst repetition rate is randomly or pseudo-randomly modulated so that bursts in the sequence of bursts have a time of occurrence relative to the nominal rate which varies over a range greater than the burst width.

In one system, the transmitter frequency is on the order of gigaHertz (e.g., 2 GHz), the burst repetition rate is on the order of megaHertz (e.g., 1 MHz), and the intermediate frequency is on the order of kiloHertz (e.g., 10 KHz). A burst may have a number of cycles on the order of 2–40 at the transmitter frequency. This produces a low duty cycle for the sequence of bursts. By modulating the time of occurrence of the sequence of bursts by more than the burst width, the likelihood that any two transmitters will generate a burst coincident with the burst of another transmitter and in a phase relationship which causes a significant response in the IF receiver is low. Also, the low likelihood that the intermediate frequency oscillators of two sensors will coincide to a degree resulting in significant interference further reduces the probability of false detection. Thus, inherent channelization of the sensor is provided, allowing multiple sensors to be used in a single field.

According to another aspect of the invention, the transmitter frequency is modulated by changing the transmitter frequency between a first frequency and a second frequency at the intermediate frequency. The first frequency relates to this second frequency such that the phase of pulses at the end of the burst at the first frequency differs from the phase of pulses at the end of the burst at the second frequency by less than one cycle, and preferably by about ½ cycle. The intermediate frequency signal generated by the mixer will indicate the relative magnitudes of the reflections at the first frequency and the second frequency. These relative magnitudes are a function of the difference in phase between the pulses at the beginning and end of a burst at the first frequency and the difference in phase at the beginning and end of a burst at the second frequency at the receiver, and by the magnitude of the reflection. Because the difference in phase at short range is much less than the difference in phase at the maximum range, the sensitivity of the device at close range is reduced relative to the sensitivity at the sensor maximum range.

Accordingly, a transmitter may be typically centered at 2.0 or 6.5 GHz, or higher, to transmit an RF burst with a burst width that is equal in time to the two-way time of flight at the maximum detection range. Since the transmitted burst is used for the receive mixer (so-called homodyne operation), there is no mixing action if the reflected signal comes back after the transmitter has stopped transmitting. Thus, the width provided by the burst width control of the transmitter controls the maximum detection range. The burst repetition rate is noise modulated in a preferred system to prevent coherent collisions with other sensors, and to prevent beat frequencies with RF interference. This is facilitated by integrating a large number of received bursts in a lowpass filter. Typically, the burst repetition rate is on the order of 1 megahertz and, the lowpass filter has a 10 millisecond response to integrate about 10,000 bursts to facilitate the channelization.

The receive mixer may be a single diode circuit followed by a bipolar transistor amplifier for low noise operation. Due to the low duty cycle of the sensor in a preferred application, the receiver functions as a sample and hold circuit to stretch the detected signal from one burst repetition cycle to the next.

Low duty cycle operation reduces total RF emission levels to the point that operation under Federal Communications Commission (FCC) part 15 regulations is possible, opening large spectral regions for use and eliminating the need for tight frequency control. Another aspect of low duty cycle operation is low power consumption. If the burst width is 10 nanoseconds, the repetition interval is 10 µs, the transmit current is reduced a thousand-fold, permitting multi-year continuous operation on batteries.

Another novel feature is provided by the frequency modulation of the transmitting oscillator, which periodically shifts the transmit frequency at the intermediate frequency of, for instance, 10 KHz. This causes a square wave to appear in the intermediate frequency at the mixer output. An intermediate frequency amplifier coupled to the receive mixer cannot pass frequencies at the burst repetition rate or at DC, and responds to changes in the average received echoes which vary with the emitted frequencies. Tying in with the homodyne operation for close returns, there is very little effect induced by the frequency modulation on the reflected signal, and there is little intermediate frequency signal to be amplified. For distant returns at near the maximum range, the frequency modulation is set to provide a full ½ cycle shift in the received echoes at the two frequencies, or in the total number of RF cycles included within the burst width. Thus, targets at the maximum range provide a Doppler response with a full 180° phase reversal between the first and second frequencies of the modulation. Since the intermediate frequency amplifier passes signals that vary at the modulation rate, and with an amplitude that corresponds to the magnitude of the phase reversal, there is no sensitivity at zero range, and maximum sensitivity at the maximum range compensating for the natural loss in sensitivity with increasing range.

A second range-defining mode transmits two radio frequency bursts, where the time spacing between the bursts defines the maximum range divided by two. The first transmitted RF burst propagates out to a target, and after a time lapse, echoes back to the sensor. The sensor generates a second RF burst after the same time lapse, and a mixing action occurs between the second pulse and the echo pulse that results in a range-gated detection process. Echoes that arrive after the second RF burst are not mixed in the detector, and thus, the sensor is not responsive to these outlying echoes. This mode maintains constant radiated power levels independent of range setting, particularly when set to long detection ranges. This can be a critical factor in meeting FCC and other regulatory agency emission limits for applications requiring long detection ranges. In comparison, the emitted pulse width in the previous mode defines the range as well as the average emitted power (average emission power is directly proportional to range).

Accordingly, an improved field disturbance sensor has been provided, which is range gated, allows for multiple sensors in a single field, and which overcomes the hypersensitivity at close range of the prior art. Furthermore, the system is simple to manufacture, low cost, and operates with such low power that multi-year battery operation is possible.

Other aspects and advantages of the present invention can be seen upon review of the figures, the detailed description, and the claims which follow.

DETAILED DESCRIPTION

A detailed description of embodiments of the present invention is provided below with respect to the figures.

Figure 1:
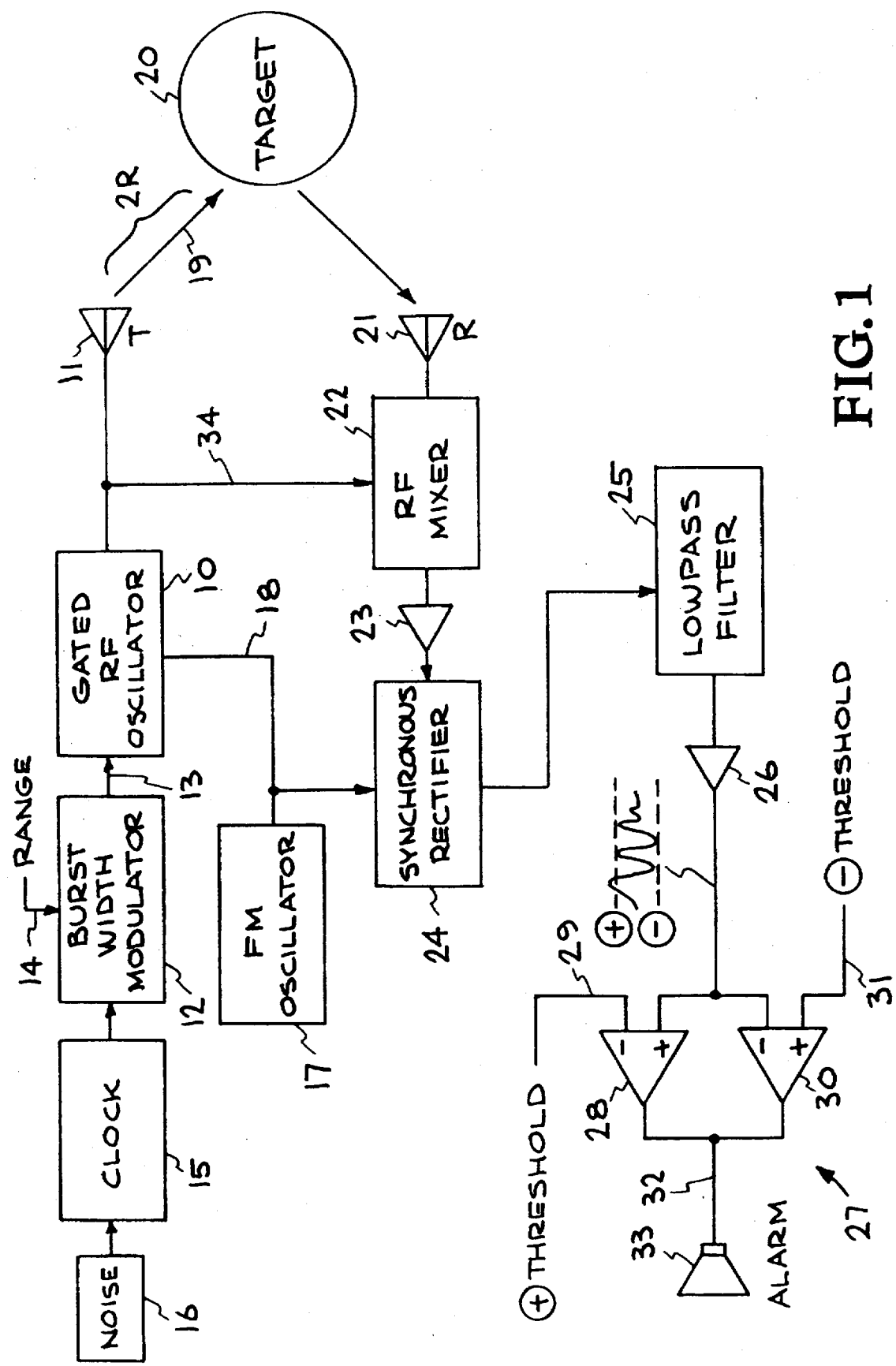
FIG. 1 is a block diagram of the range-gated field disturbance sensor of the present invention.

FIG. 1 is a block diagram of a range-gated field disturbance sensor with range sensitivity compensation according to the present invention. The basic system includes a gated RF oscillator 10 which drives a transmitting antenna 11. The gated RF oscillator 10 generates a sequence of bursts having a burst width determined by a burst width modulator 12 which is connected across line 13 to the gated RF oscillator. The burst width modulator 12 defines a burst width in response to an input control 14 to select the range of the device. The burst repetition rate is determined by a clock 15 which drives the burst width modulator. Clock 15 is phase modulated by a random source 16, such as noise which may be amplified to produce a modulation signal, or may be inherent in the burst repetition rate oscillator. Also, pseudo random modulation may be used.

The gated RF oscillator 10 is frequency modulated by an intermediate frequency source 17 connected to the gated RF oscillator 10 across line 18.

The transmitted burst 19 reflects off a target 20 and the echo is detected by a receive antenna 21. The receive antenna 21 drives an RF mixer 22, which is also coupled to the transmitted signal, as schematically illustrated by line 34. The output of the RF mixer 22 is coupled to an intermediate frequency amplifier 23 which is tuned to the frequency of the FM intermediate frequency source 17. The output of the intermediate frequency amplifier 23 is coupled to a synchroonous rectifier 24, which is synchronized by the FM intermediate frequency source 17. The output of the rectifier 24 is supplied through a lowpass filter 25 and baseband amplifier 26 to a threshold detection circuit, generally 27. The threshold detection circuit comprises a first comparator 28 having a negative input coupled to a positive threshold value 29, and a positive input coupled to the output of the baseband amplifier 26. Also, the threshold detector includes a second comparator 30 having a negative input coupled to the output of the baseband amplifier 26 and the positive input coupled to the negative threshold 31. When the amplitude of the output of the baseband amplifier 26 exceeds the thresholds, an alarm signal is supplied on line 32 to drive an alarm circuit, such as a beeper 33 or other responding apparatus. The beeper 33 may be replaced, for instance, by a switch which drives a wide variety of responding apparatus.

Also, rather than driving a threshold detection/alarm circuit, as illustrated in FIG. 1, the output of the baseband amplifier may be digitized and processed to determine the characteristics of the disturbance shown in the received signals, such as velocity of motion, size, etc.

In one designed system, the gated RF oscillator generates a burst of about 2 gigahertz. The FM oscillator 17 operates at about 10 KHz, and modulates the output frequency of the oscillator 10 between, for instance, 2.00 GHz and 2.10 GHz. The burst repetition frequency defined by the oscillator 15 in this embodiment is about 2 MHz. The noise source 16 preferably modulates the phase of the burst repetition frequency oscillator 15 over an equivalent range substantially greater than the burst width.

The burst width defines the range of the device, because RF mixing at the mixer 22 only occurs during transmission of the burst. In the 2 GHz system mentioned above, the burst width may be on the order of 2 to 40 cycles or so of the gated RF oscillator 10, providing a low duty cycle for the transmitter, and therefore a low power consumption. At a 2 GHz transmitter frequency, and a range of about 12 inches, the burst width should be about 4 cycles, or about 2 nanoseconds.

Figure 2:
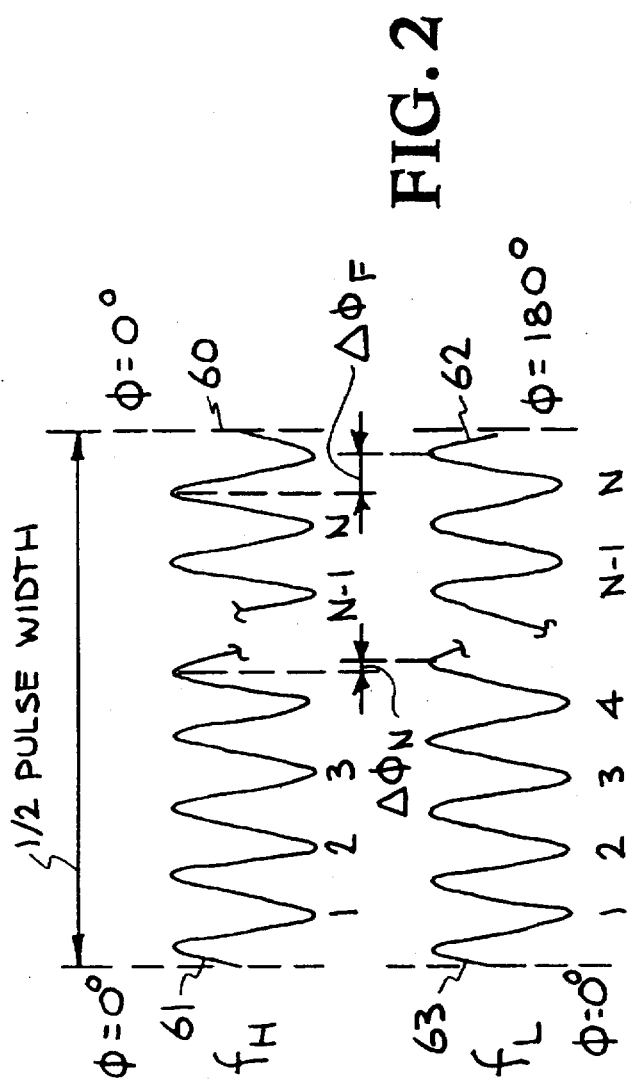
FIG. 2 is a timing diagram illustrating the frequency modulation features of the present invention.

FIG. 2 illustrates certain characteristics of the bursts in the sequence of bursts. As illustrated in FIG. 1, the RF oscillator is frequency modulated with a square wave at approximately 10 KHz. Thus, the burst will be generated with a first low frequency $f_L$, and a second high frequency $f_H$. Frequencies are only slightly different from one another as illustrated in FIG. 2. Thus, in the near range, such as after four cycles, the difference in phase at a given distance between the two frequencies ($\Delta\phi_N$) is very slight. However, at the end of the burst, the difference in phase at the end of the burst between the two frequencies ($\Delta\phi_F$) is about 180°. Thus, the head 60 of the burst at frequency $f_H$ is about in phase with the tail 61 for a given burst width for a relative phase shift of about 0°. In contrast, the head 62 of the burst at frequency $f_L$ is about 180° out of phase with the tail 63 for a relative phase shift of about 180° at the same burst width. This provides a full 180° phase reversal at the intermediate frequency in the echo received from objects at the maximum range based on the 180° relative phase shift difference.

The sensor, according to a preferred embodiment, has a relative phase shift difference of less than 360° and, for best results, less than about 180°, between the two RF frequencies at the maximum sensor range.

The sensors, according to the present invention, are operational even with a relative phase shift difference of more than one cycle. However, when the relative phase shift difference is greater than 180°, the sensitivity of the device will be reduced. Also, if the relative phase shift difference at a particular range falls to zero, then blind spots may be created within the sensor field. Thus, in the preferred system, which has an adjustable burst width, the frequency modulation is set so that at maximum range the relative phase shift difference is about 180°, so that as the range is tuned by shortening the burst width, the relative phase shift difference is less than 180°. For very short range operation, the relative phase shift difference will be slight. The particular relation selected for a given design will depend on the characteristics of the field in which the sensor is deployed, and the components used to implement the sensor.

Thus, for instance, there may be N cycles at the transmitted frequency $f_L$, for a given burst width. For this embodiment, at the transmitted frequency $f_H$, there may be N+½ cycles in the burst width for the higher frequency. Of course, the absolute number of cycles in a burst will vary depending on the circuits used to generate the bursts. But the phase relationship can be enforced by controlling the transmitter frequency.

Figure 3:
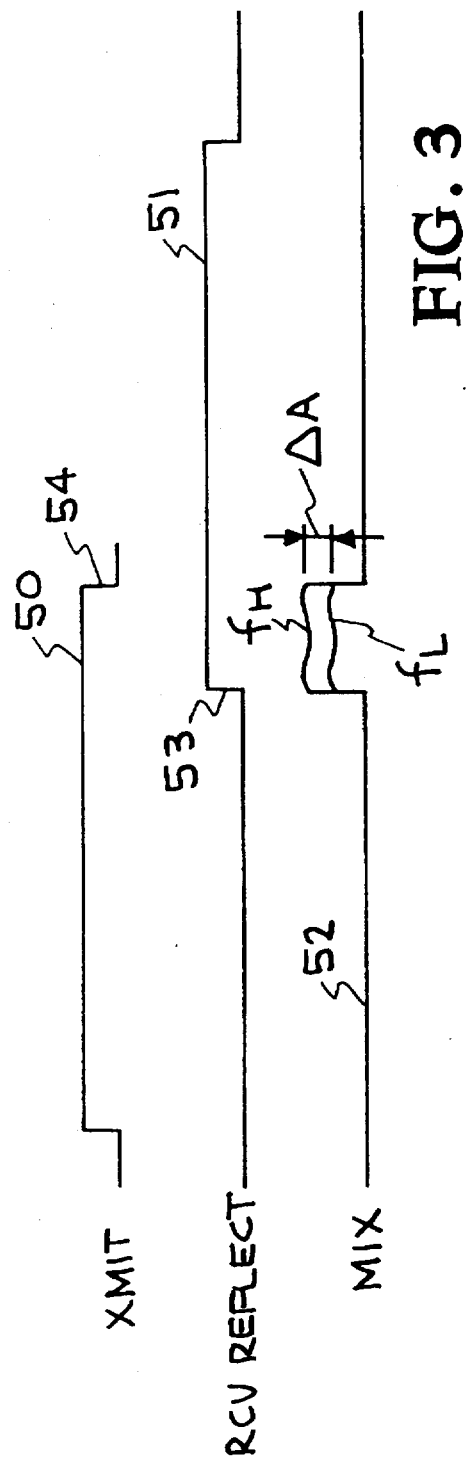
FIG. 3 is a timing diagram illustrating the mixing and range-gating operation of the present invention.

FIG. 3 illustrates the mixing function of the received cycle. Thus, in FIG. 3, the trace 50 illustrates the transmitted burst. The trace 51 illustrates a receive reflection. Trace 52 illustrates the period during which mixing occurs. That is, mixing occurs from the beginning of the reception of the reflected signal at point 53 until the end of the transmitted signal at point 54.

Also illustrated at trace 52 are the magnitudes of the received echoes at the low frequency $f_L$ and at the higher frequency $f_H$. This difference in amplitude $\Delta A$ is a function of the distance at which the disturbance occurs as reflected in the difference in phase between the transmitted burst and the received reflections, as well as the magnitude of disturbance. In the actual system, the intermediate frequency signal is based on integrating a large number of the mixed signal pulses, oscillating between the $f_H$ and $f_L$ values at the intermediate frequency. Thus, at very close ranges, the differences in magnitude due to the frequency modulation for a given magnitude of disturbance will be lower than the difference in magnitude of the mixed signal at longer range.

Figure 4:
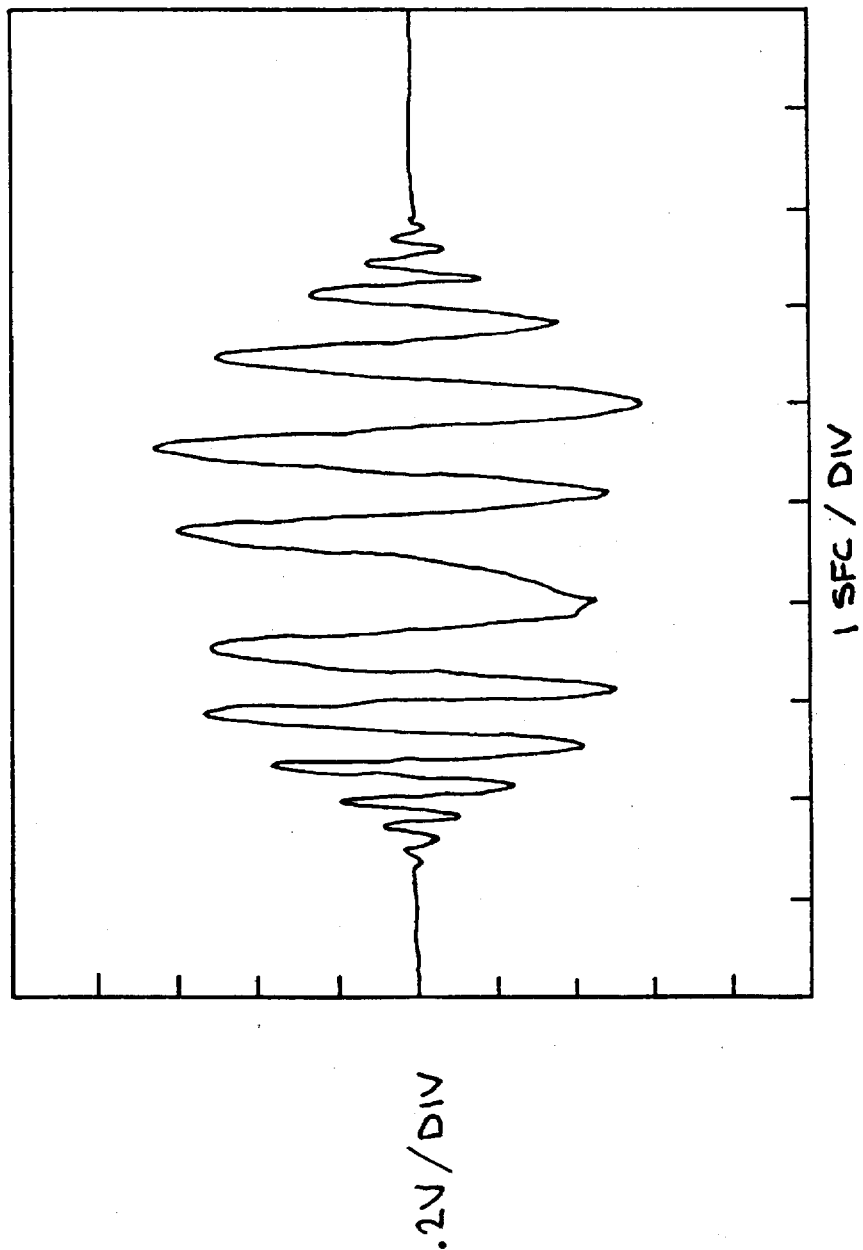
FIG. 4 is a plot showing the performance of the sensor according to the present invention.

FIG. 4 illustrates the performance of the sensor over its set range, showing that the sensitivity does not increase substantially at close range. Thus, in FIG. 4, the intermediate frequency response sampled at the output of the baseband amplifier 26, for instance, is illustrated. With the range set at about 12 inches, this signal was generated by moving a hand in to touch the transmitter and then back out. As can be seen at the close range at point 70, the amplitude of the signal is not substantially greater than at about 6 inches at point 71. FIG. 4 also illustrates that outside the range, there is little intermediate frequency signal generated.

Figure 5:
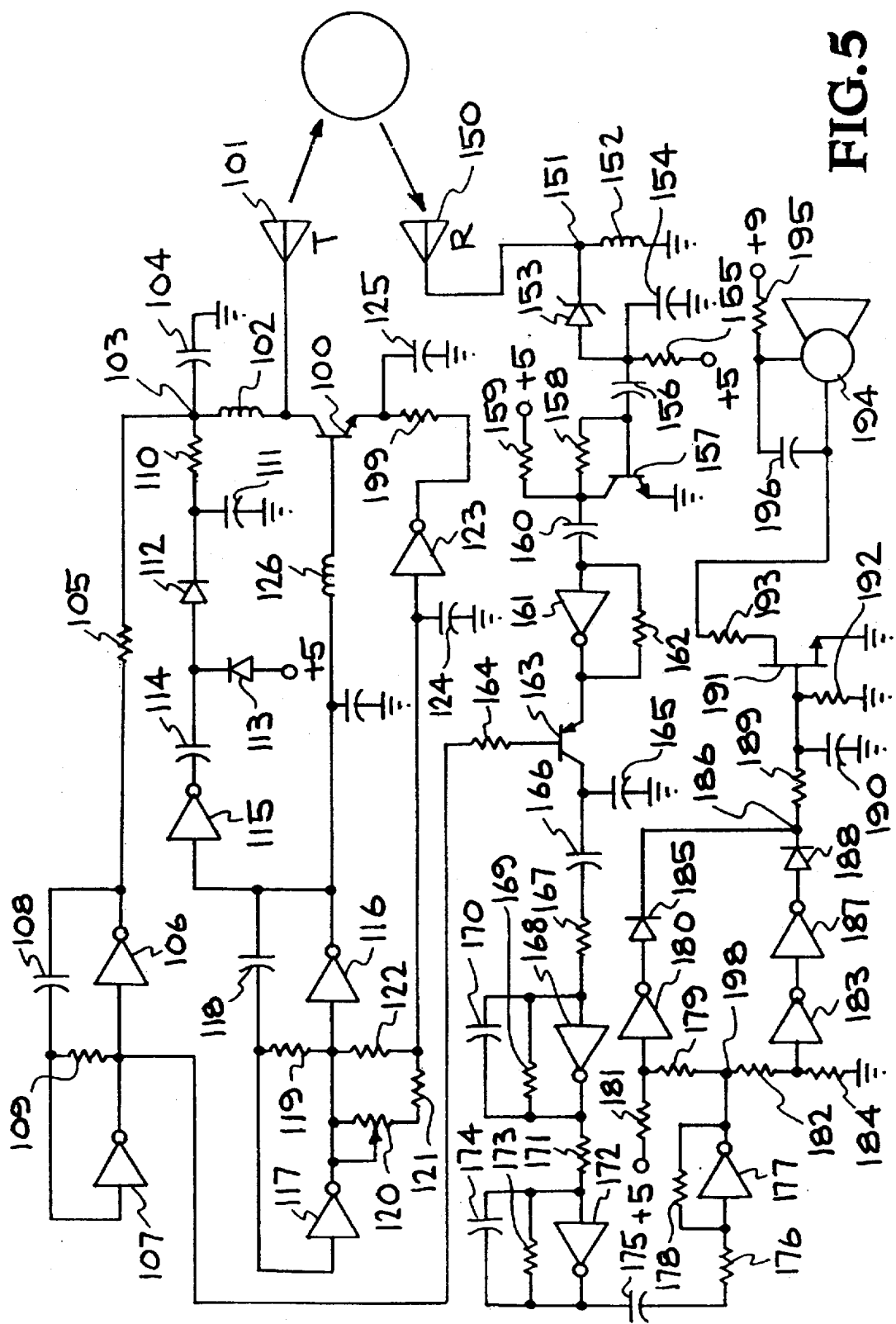
FIG. 5 is a schematic diagram of one embodiment of the sensor according to the present invention.

FIG. 5 is an electrical schematic diagram of a sensor according to the present invention which was used in generation of the plot of FIG. 4. The transmitter is driven by a radio frequency transistor 100 which is biased to oscillate at the transmitter frequency. The collector of the transistor 100 is coupled to antenna 101, and across an inductance 102 (simply inherent in the physical layout) to bias node 103. The bias node 103 is coupled across a capacitor 104 to ground, and through resistor 105 to an FM oscillator composed of inverter 106 and inverter 107. The inverter 106 drives the output of the FM oscillator, and is connected in feedback across capacitor 108 to the input of inverter 107. Also, the output of inverter 107 is coupled across resistor 109 to its input.

Node 103 is also connected across resistor 110 to capacitor 111 which is coupled on its opposite terminal to ground. The cathode of diode 112 is coupled to the capacitor 111, and its anode is coupled to the cathode of diode 113. The anode of diode 113 is coupled to a 5 volt supply. Also, the anode of diode 112 and the cathode of diode 113 are coupled across capacitor 114 to the output of inverter 115. The input of inverter 115 is coupled to the burst repetition frequency oscillator set at about 2 MHz, composed of inverter 116 and inverter 117. The output of inverter 116 is coupled to the input of inverter 115, and across capacitor 118 to the input of inverter 117. Also, the output of inverter 117 is connected across resistor 119 to its input.

A variable resistance composed of potentiometer 120 in series with resistor 121, and parallel resistor 122 are coupled from the output of inverter 117 to the input of inverter 123. Also, the input of inverter 123 is connected across capacitor 124 to ground. The output of inverter 123 is connected across resistor 199 to the emitter of the oscillating transistor 100. Also, capacitor 125 is connected from the emitter of transistor 100 to ground.

The base of transistor 100 is driven through inductor 126 by the output of inverter 116 at the burst repetition rate frequency.

In operation, the frequency of oscillation of the transistor 100 is varied by the bias at node 103. This bias is modulated at 7 Khz by the oscillator composed of inverters 107 and 106. The transistor 100 oscillates when the base to emitter voltage is above its threshold. This occurs on the rising edge of the output of inverter 116 for short burst length determined by the delay induced by the RC network composed of resistors 120 through 122 and capacitor 124, as driven through inverter 123. Thus, when the output of inverter 123 rises, the difference in voltage between the base and emitter of transistor 100 falls below the threshold, turning off the oscillator. Thus, on the rising edge of the output of inverter 116, a short burst is emitted by antenna 101 having a burst length which can be adjusted by adjusting potentiometer 120. Thus, this circuit sets the burst length for the transmitter circuit. Unwanted variations in burst width are minimized when inverters 116 and 123 are matched through common monolithic integration. With a 2 MHz burst repetition rate and a 7 Khz frequency modulation rate, there are about 6500 bursts per IF cycle.

The receiver includes receiving antenna 150 which is coupled to node 151. From node 151, an inductor 152 is coupled to ground. Also, the cathode of Schottky diode 153 is coupled to node 151. The anode of diode 153 is connected across capacitor 154 to ground and across resistor 155 to a positive 5 volt supply, and is coupled through capacitance 156 to an intermediate frequency transistor 157 connected as an amplifier. Thus, the base of transistor 157 is connected across resistor 158 to its collector. Also, the collector is coupled across resistor 159 to a 5 volt supply. The emitter of transistor 157 is connected to ground. The collector of transistor 157 is connected through capacitor 160 to an intermediate frequency amplifier composed of inverter 161 with resistor 162 connected in feedback. The output of inverter 161 is connected to a sample and hold circuit composed of transistor 163 having its base connected across resistor 164 to the output of inverter 107 in the FM oscillator.

The collector of transistor 163 is connected to a first terminal of capacitor 165. The second terminal of capacitor 165 is connected to ground. Also, the collector of transistor 163 is connected through capacitor 166 and resistor 167 to the input of inverter 168 which is connected as a baseband amplifier. The resistor 169 and capacitor 170 are connected in parallel and in feedback across inverter 168. The output of inverter 168 is connected across resistor 171 to the input of inverter 172 which is connected as an amplifier with resistor 173 and capacitor 174 in parallel and in feedback. The output of inverter 172 is connected through capacitor 175 and resistor 176 to the input of inverter 177. Resistor 178 is connected in feedback across inverter 177. The output of inverter 177 drives a threshold detection circuit. The input of the threshold detection circuit is node 198. A first resistor 179 is coupled between node 198 and the input of inverter 180. Also, resistor 181 is connected between the input of inverter 180 and a 5 volt supply. A second resistor 182 is connected between node 178 and inverter 183. Also, resistor 184 is connected between the input of inverter 183 and ground. The output of inverter 180 is connected through diode 185 to node 186. The output of inverter 183 is connected through inverter 187 and diode 188 to node 186. Node 186 is connected across RC network composed of resistor 189 and capacitor 190 to the gate of transistor 191. Also, resistor 192 is connected between the gate of transistor 191 and ground. The source of transistor 191 is connected to ground, the drain of transistor 191 is connected through resistor 193 to a beeper 194 which is biased with resistor 195 and bypassed with capacitor 196.

Thus, in operation, the transmitted signal is coupled to the receiving antenna by proximity of the transmitter and receiver. The reflected signal is received by the receive antenna and mixed at diode 153. Each cycle of the mixed signal is sampled by diode 153, and charges capacitor 154 to the magnitude of the sampled signal. The magnitude of the voltage on capacitor 154 will vary at the intermediate frequency as described above. This intermediate frequency signal is coupled through the amplifier composed of transistor 157 and inverter 161 to the sample and hold circuit driven by transistor 163. The transistor 163 is synchronized with the modulation frequency of the transmitter to sample and hold the average magnitude of the mixed signal. The average magnitude is amplified and supplied to a peak detection circuit. By setting the trip value on the peak detection circuit, the sensitivity of the sensor can be selected.

In the preferred system, the transmitting and receiving antennae 101 and 150 are formed with 1½ inch lengths of wire arranged in a dipole for a 2 GHz transmitter frequency, and positioned so that the transmitted signal is coupled to the receiving antenna with a magnitude sufficient for the mixing operation.

The burst repetition frequency generator is modulated by noise inherent in the inverters selected for the embodiment illustrated in FIG. 5, so no additional modulation circuitry is necessary.

With the component values illustrated in the figure, this circuit is range tunable from about zero to about 12 feet. The modulation of the RF oscillator is set for approximately 180° phase reversal at the maximum range.

Figure 6:
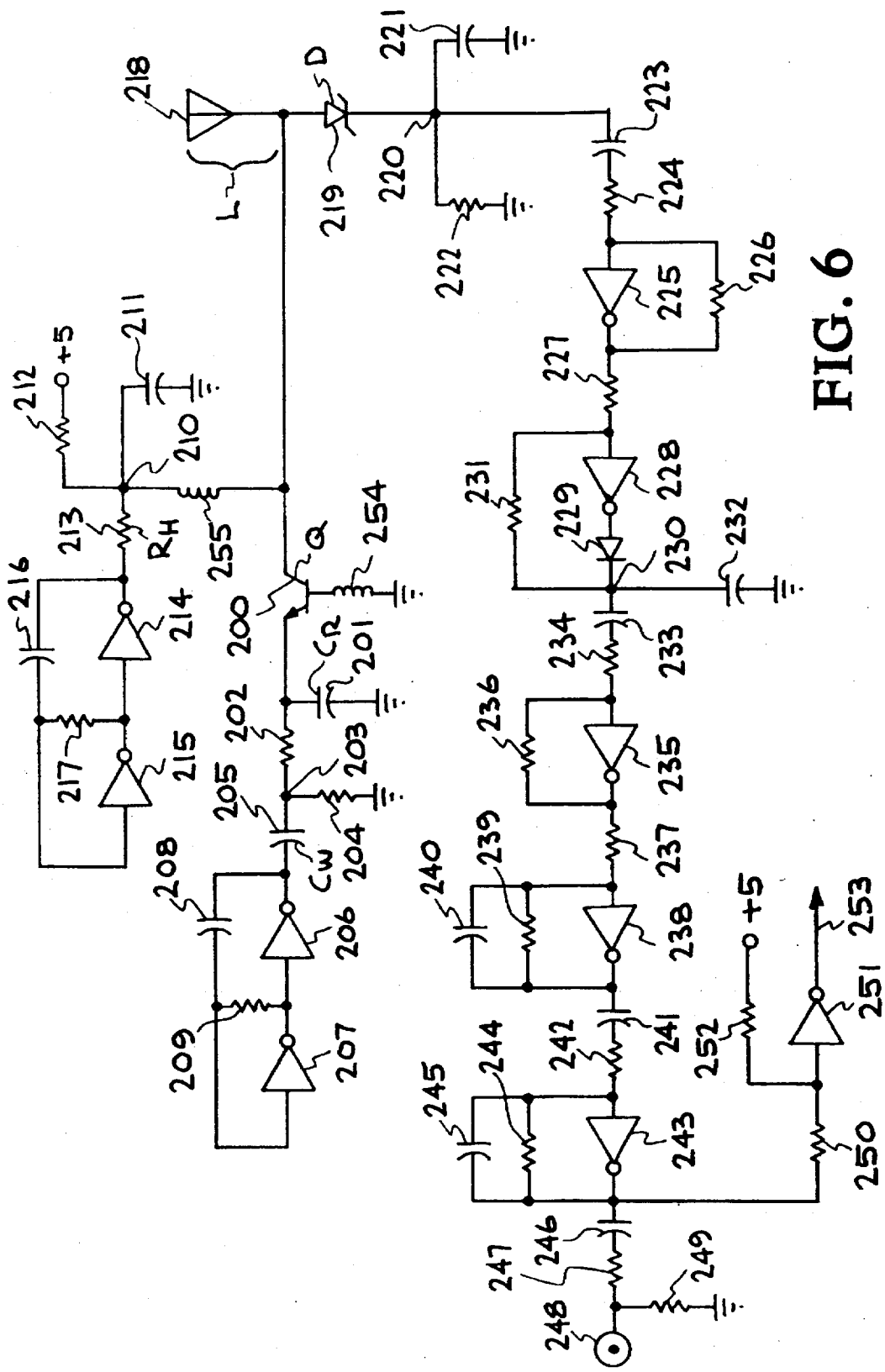
FIG. 6 is a schematic diagram of an alternative embodiment of the sensor according to the present invention.

FIG. 6 illustrates an alternative embodiment of the range-gated proximity sensor according to the present invention. In this embodiment, the RF oscillator is driven by transistor 200. The base of transistor 200 is connected to ground through inductor 254. The emitter of transistor 200 is connected across capacitor 201 to ground and across resistor 202 to node 203. Node 203 is connected across resistor 204 to ground and across capacitor 205 to a 2 MHz burst repetition rate oscillator. This oscillator includes inverter 206 and inverter 207 connected in series. The output of inverter 207 is connected to capacitor 205, and across capacitor 208 to the input of inverter 207. Also, the output of inverter 207 is connected across resistor 209 to its input.

The collector of transistor 200 is modulated through inductor 255 by the signal at node 210 which is connected across capacitor 211 to ground and across resistor 212 to a 5 volt supply. Also, node 210 is connected across resistor 213 to the output of the modulating oscillator which is composed of inverters 214 and 215 in series. The output of inverter 214 is connected across capacitor 216 to the input of inverter 215. Also, the output of inverter 215 is connected across resistor 217 to its input.

The receiver shares the antenna 218 which is driven by the oscillator 200. Thus, the receiver comprises Schottky diode 219 having its anode connected to antenna 218. The cathode of diode 219 is connected to node 220. Capacitor 221 is connected from node 220 to ground. Resistor 222 is connected from node 220 to ground. Also, node 220 is connected through capacitor 223 and resistor 224 to an amplifier composed of inverter 225 with resistor 226 connected in feedback. The output of inverter 225 is connected across resistor 227 to the input of inverter 228. The output of inverter 228 is driven through diode 229 to node 230. Resistor 231 is connected from node 230 to the input of inverter 228. Also, capacitor 232 is connected from node 230 to ground. Node 230 is connected through capacitor 233 and resistor 234 to the input of inverter 235. The voltage at node 230 is the peak detected value of the IF signal supplied by IF amplifier 225. Resistor 236 is connected in feedback from the output of inverter 235 to its input. Also, the output of inverter 235 is connected across resistor 237 to the input of inverter 238. The output of inverter 238 has resistor 239 and capacitor 240 coupled in parallel and in feedback. The output of inverter 238 is connected through capacitor 241 and resistor 242 to the input of inverter 243. Inverter 243 has resistor 244 and capacitor 245 connected in feedback. The output of inverter 243 is connected through capacitor 246 and resistor 247 to node 248. Node 248 is also connected across resistor 249 to ground. Also, the output of inverter 243 is connected through resistor 250 to the input of inverter 251. The input of inverter 251 is connected across resistor 252 to the positive supply. The output of inverter 251 is a signal on line 253 indicating detection of a disturbance in the field. Also, node 248 may be used to drive such alarm circuitry as desired.

Figures 7, 8:
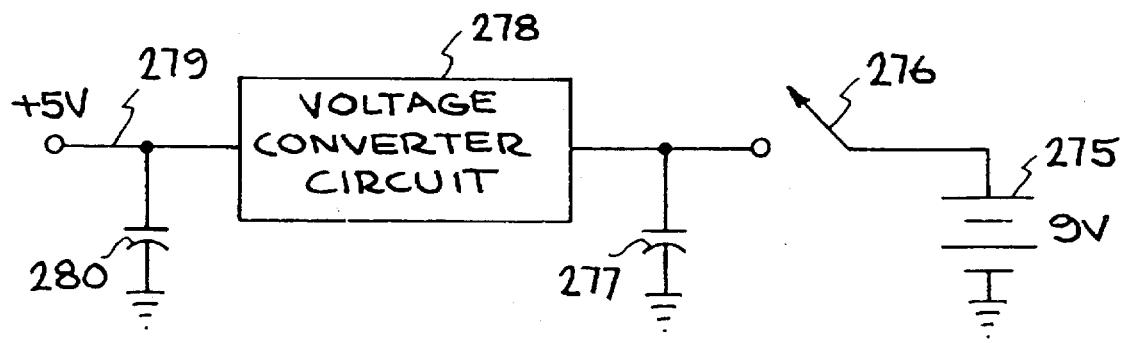
FIG. 7 is a schematic diagram of a battery power supply for use with the circuit of FIG. 6.
FIG. 8 is a table of component values of FIG. 6 at two transmitter frequencies.

This circuit of FIG. 6 is driven by a power supply such as shown in FIG. 7. Thus, a 9 volt battery 275 is connected through a power switch 276 to a converter circuit which includes capacitor 277 coupled from the switch 276 to ground, and a voltage converter circuit 278 having an output 279 of about 5 volts. Also, the output 279 is connected across capacitor 280 to ground. The 5 volt supply is used to drive the circuitry illustrated in FIG. 6.

The frequency of the transmitter can be adjusted as suits the needs of a particular design. For a 2 GHz center frequency, the values of labelled components are illustrated in FIG. 8. Also, for a 6.5 GHz center frequency, values illustrated in FIG. 8 can be used.

The circuit designs illustrated in FIGS. 5 and 6 are composed of off-the-shelf components readily available to persons of skill in the art, examples of the values of which are shown in the figures. It will be recognized that these circuits may be provided in application specific integrated circuits (ASICs), or in other combinations of components as suits the needs of a particular designer.

The embodiments described herein have RF transmitters which are frequency modulated at an intermediate frequency. Alternative systems may have amplitude modulated RF transmitters, or transmitters modulated by other methods, using techniques known in the art of oscillator modulation. For instance, the RF oscillator may be operated in a double burst mode, where a first burst is transmitted followed by a second burst with a fixed interval in between. The first burst will mix with the second only at a specific range determined by the inter-burst interval. This will save average power output for longer ranges, while preventing disturbances at closer ranges from being measured. Also, other envelope shaping techniques could be employed for various effects.

Figure 9:
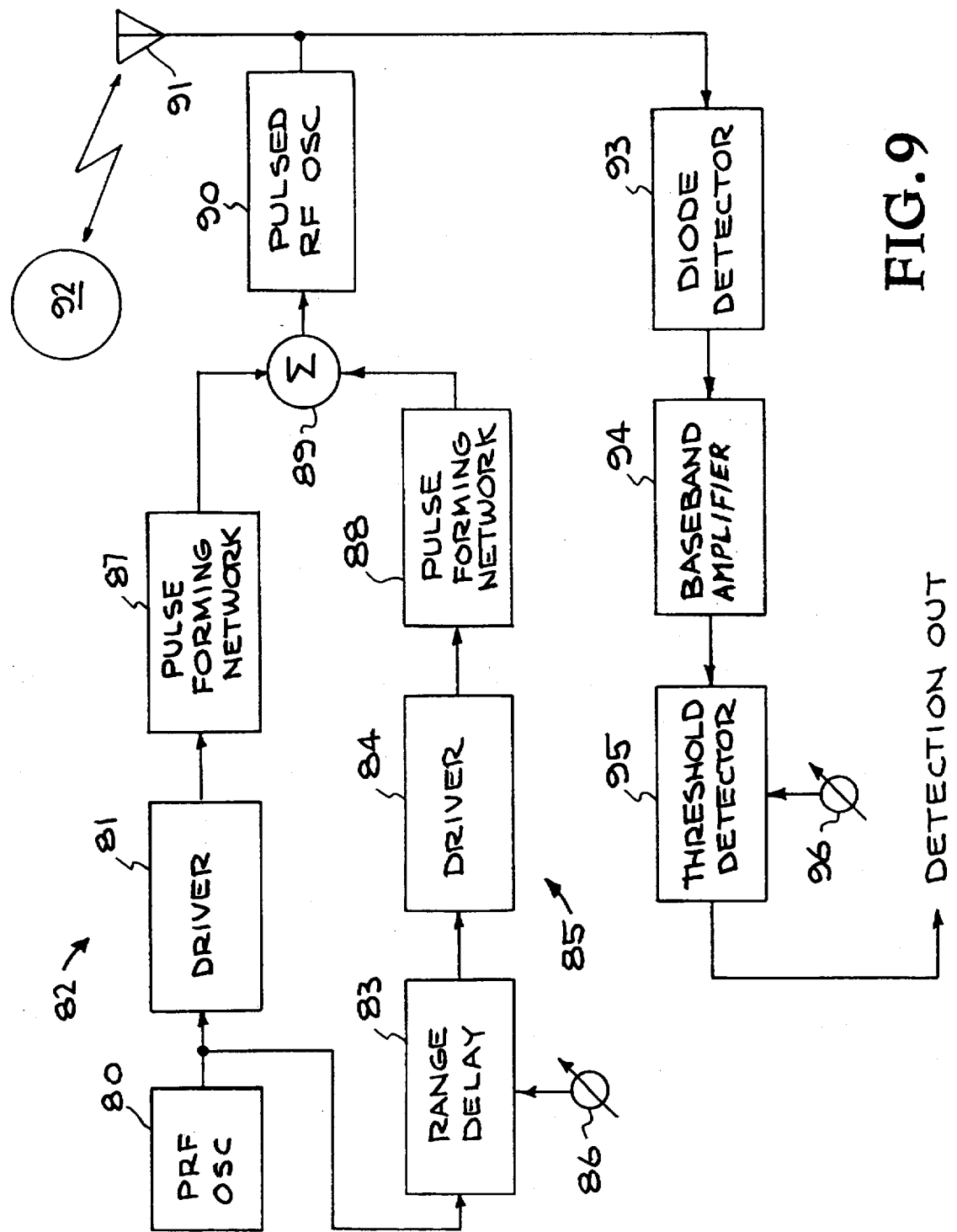
FIG. 9 is a block diagram of another embodiment of the sensor according to the present invention.

Referring to FIG. 9, a pulse repetition frequency or PRF oscillator 80 supplies square waves to a driver 81 in a first path 82. The square waves from PRF oscillator 80 also pass through a delay 83 to a driver 84 in a second path 85. Delay 83 is an adjustable range delay which sets the range and is set by range adjustment 86. The two drivers 81, 84 are connected to respective pulse forming networks (PFNs) 87, 88 that change the square waves into impulses. Thus a pulse from PRF oscillator 80 produces an impulse from PFN 88 that is delayed with respect to the impulse from PFN 87. The impulses provided by the PFNs 87, 88 are summed in a summation circuit 89 and applied to a pulsed RF oscillator 90. Thus there is an input to RF oscillator 90 whenever an impulse at either PFN 87 or 88 is produced. In response to each impulse, the RF oscillator 90 generates short bursts (pulses) of RF energy that are outputted to a single transmit/receive antenna 91. Transmitted RF pulses are propagated from antenna 91 toward an object 92, and reflected pulses (echoes) from the object are received by antenna 91.

A diode detector 93 is connected to the antenna 91 to provide mixing action between the reflected first pulse (burst) and the generated second pulse (burst). Since the generated second pulse occurs after a delay, it mixes with echoes of the first radiated pulse that arrive back at the antenna 91 after the same delay. This mixing action produces a steady DC level at the diode detector 93, as a result of averaging detected signals over many cycles of the PRF oscillator 80, until the reflecting target 92 moves. A moving target 92, at a range corresponding to the delay time divided by two, will produce a Doppler signal at the diode detector 93 as long as the target is within the range defined by the range delay 83 and the RF pulse width. Targets that lie outside this range do not produce echoes that return in time to be mixed by the second RF pulse. Therefore, this radar is range-gated.

The range delay is preferably not more than about 10% of the period of the PRF oscillator to eliminate interference effects due to range ambiguities. The PRF oscillator 80 typically operates at 2 MHz (500 ns period), although it may operate over a wide frequency range, e.g. 10 kHz–10 MHz. The range is typically about 2–100 ft, which requires a 4–200 ns delay. Thus the two RF bursts produced by each PRF cycle do not interfere with bursts from another cycle because the PRF period is much longer.

The Doppler output from the diode detector 93 is amplified by a baseband amplifier 94 that has a typical gain of about 60 dB and a bandwidth of about 0.5 to 100 Hz. The baseband amplifier 94 is connected to a threshold comparator 95, so any Doppler signal above a level defined by the sensitivity adjustment 96 is detected and used to trigger an alarm output, generally a switch closure.

Figure 10:
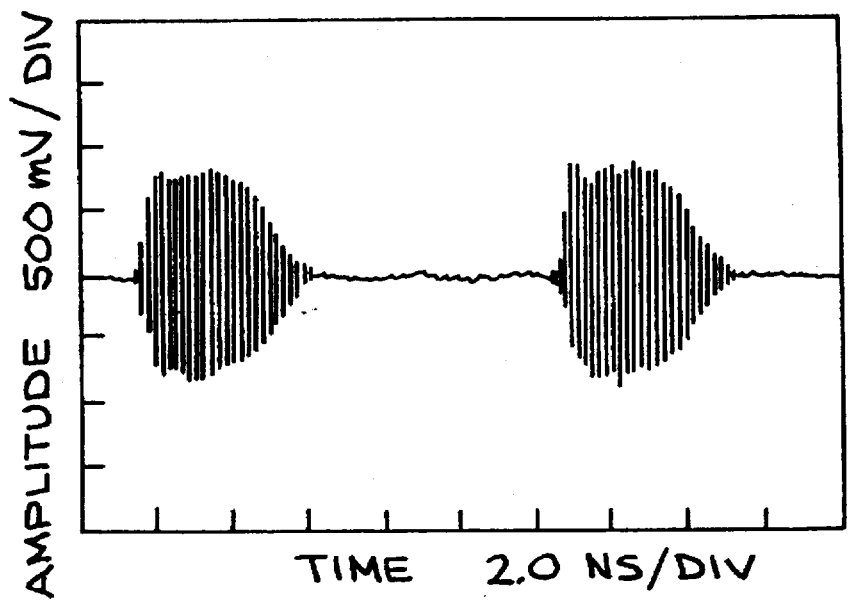
FIGS. 10A, B depict the radiated pulses and associated spectrum from the embodiment of FIG. 9.
Figure 10:
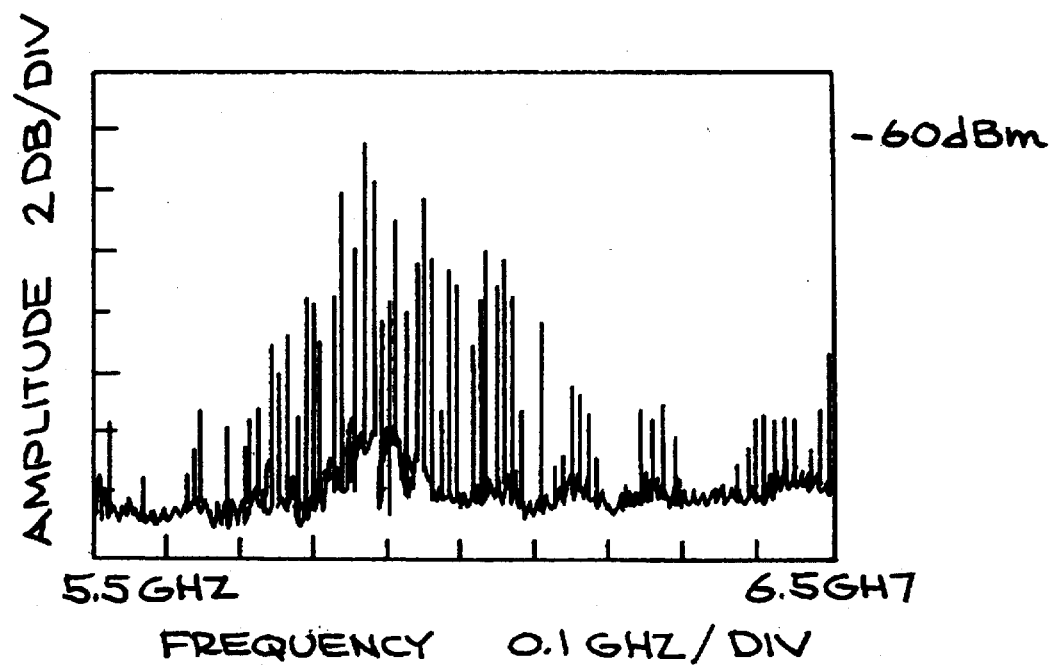

Illustrative RF pulses appearing at the antenna terminal are shown in FIG. 10A. They are 6.5 GHz bursts about 4 nanoseconds wide and separated by about 11 nanoseconds, corresponding to about 5.5 feet of two-way travel. For reference, the emission spectrum is shown in FIG. 10B, and is seen to lie within the 5.5–7.2 GHz low power device (LPD) band as defined by the FCC. FIGS. 10A, B data was taken at a range of 0.3 meters with a 14 dB gain antenna.

Figure 11:
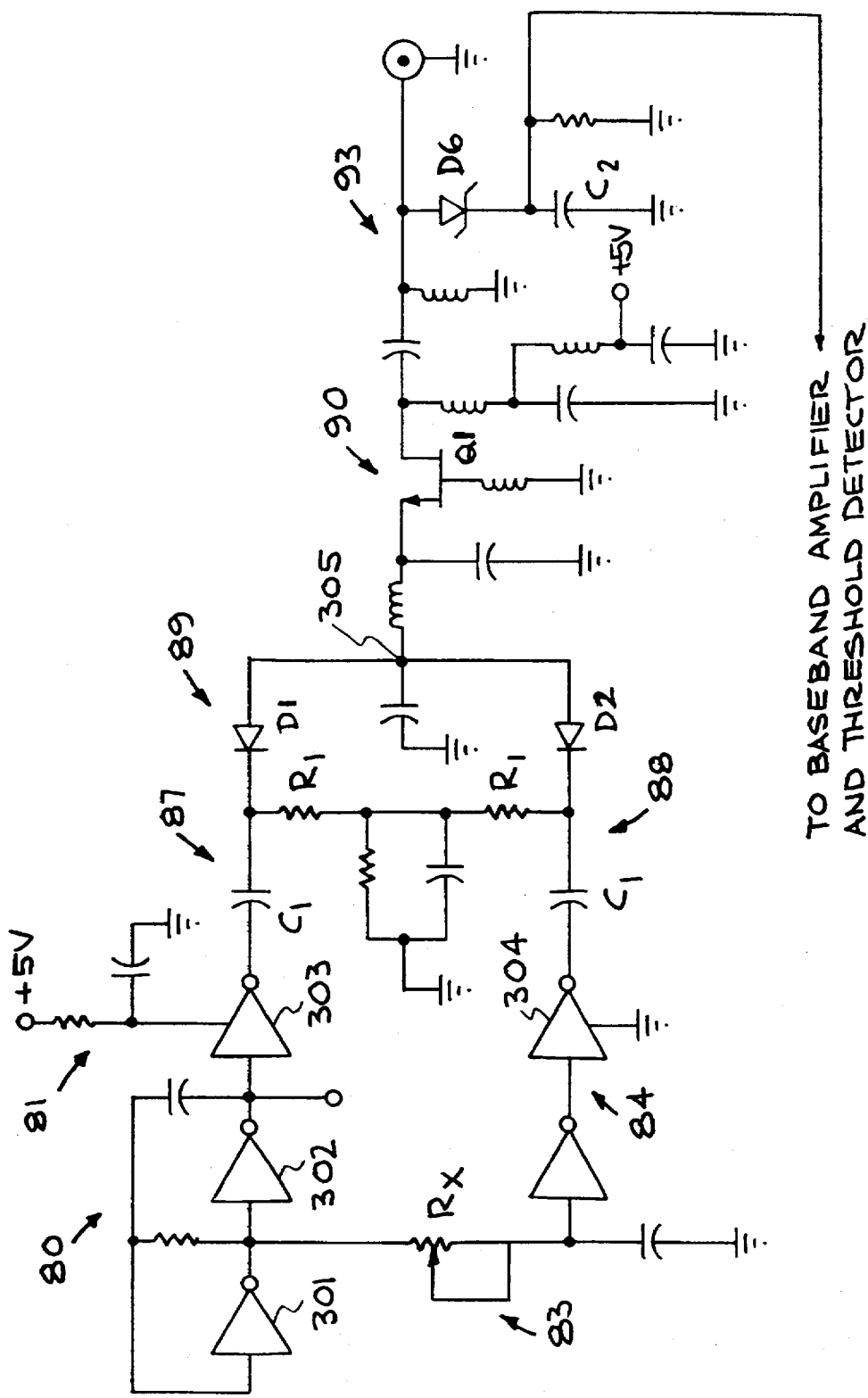
FIG. 11 is a schematic diagram of the embodiment of FIG. 9.

FIG. 11 is a schematic diagram of the radar embodiment of FIG. 9. PRF oscillator 80 is formed of a pair of inverters 301, 302, first driver 81 is formed of inverter 303 and second driver 84 is formed of inverter 304. Range delay 83 is adjusted through variable resistor $R_x$. Negative transitions from CMOS inverters 303, 304 are differentiated by PFNs 87, 88 comprised of 22 picoFarad capacitors C1 and 270 ohm resistors R1 into negative spikes several nanoseconds in width. These spikes are combined through summation diodes D1 and D2 at node 305 (summation circuit 89) and are then used to bias ON RF oscillator 90 formed of transistor Q1 which is preferably a GaAsFET. Q1 supplies RF bursts to the antenna that have a width and spacing that closely resembles the summation pulses at the D1, D2 anodes. Schottky diode D6 of detector 93 peak detects the RF burst voltage and develops a steady DC voltage across the 0.01 microFarad capacitor C2 (signal averaging circuit) connected to its cathode. This steady DC voltage represents an average over many pulses from the PRF oscillator, e.g. hundreds to thousands of pulses. When a target moves through a zone corresponding to the range defined by the second pulse, the diode's cathode voltage varies with an amplitude on the order of microvolts to millivolts and with a frequency defined by the Doppler shift produced by the target, typically 0.5 to 100 Hz for moving humans. This alternating signal is amplified and threshold detected by operational amplifiers, as is well known in the art, to produce an alarm switch closure.

The temporal location of the second RF burst may be time hopped between two or more time slots for multiple range cell operation, as described in U.S. Pat. No. 5,361,070 which is herein incorporated by reference.

The range gated field disturbance sensor according to the invention can be used for medical applications such as organ motion monitoring, e.g. respiration and/or heart rate, as described in U.S. patent application Ser. No. 08/287,746 which is herein incorporated by reference.

This radar embodiment differs from other range-gated radars (like airport radars) in that it uses a single transistor to transmit the pulse and to generate the receive mixer pulse, a single transmit/receive antenna, a simple detector diode connected to the antenna, and an averaging circuit connected to the diode to produce an average signal over many pulses. This range-defining embodiment transmits two radio frequency bursts, where the time spacing between the bursts defines the maximum range. The delayed pulse to the mixer is generated by the same RF transistor as the first RF pulse which is propagated to the object and produces a reflected pulse which is combined in the mixer with the delayed pulse. The design is efficient and low cost because only a single transistor, a single antenna, and a single diode are used.

CONCLUSION

Accordingly, the present invention provides a field disturbance sensor which is precisely range-gated, immune from interference from neighboring sensors of the same type, or from other sources of noise, and has compensation against hypersensitivity at close range. Further, the circuit is very low power, enabling battery operation with long life. Thus, a wide variety of new applications is provided for microwave based proximity sensors, including, by way of example, proximity sensing car alarms, home security systems, keyless entry systems, backup warning radar, and the like.

The system is range-gated to limit the maximum detection range to reduce false alarms with a typical adjustment range for the current embodiments of 6 inches to 12 feet. The burst repetition frequency is noise coded to allow co-location of multiple sensors. The receiver is very sensitive, allowing reduced transmit power. Thus, it need not operate in the ISM bands which are crowded with other high powered microwave users, such as microwave ovens. This results in a low operation current with multiple year battery life possible, and very low manufacturing costs. The low manufacturing cost is in part due to the low transmitted power which avoids complex circuitry to comply with communications regulations. Furthermore, the system is range sensitivity compensated, eliminating the $1/R^2$ characteristic of prior art systems. Thus, the system is not hypersensitive at close range and maintains fairly constant sensitivity from 0 to the maximum range.

A second range-defining mode, the pulse homodyne field disturbance sensor, transmits two radio frequency bursts, where the time spacing between the bursts defines the maximum range divided by two.

The foregoing description of preferred embodiments of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A sensor comprising:
   a PRF oscillator for producing a sequence of PRF pulses having a PRF period;
   a first impulse generator connected to the PRF oscillator for generating a first impulse from each PRF pulse;
   an adjustable range delay connected to the PRF oscillator and producing a fixed delay;
   a second impulse generator connected to the adjustable range delay for generating a second impulse from each PRF pulse, the second impulse being delayed from the first impulse by the fixed delay;
   a summation circuit connected to the first and second impulse generators;
   a single transistor pulsed RF oscillator connected to the summation circuit for producing a pair of RF bursts from each PRF pulse, a first burst from the first impulse and a second burst from the second impulse, the second burst being delayed from the first burst by the fixed delay;
   a single transmit/receive antenna connected to the pulsed RF oscillator for transmitting the first burst toward an object and receiving reflected pulses from the object;
   a single diode detector connected to the pulsed RF oscillator and the transmit/receive antenna for mixing reflected pulses produced by the first burst with the second burst to produce a detected signal.

2. The sensor of claim 1 wherein the single diode detector further comprises a signal averaging circuit for averaging the detected signals produced by a plurality of PRF pulses.

3. The sensor of claim 1 wherein the signal averaging circuit comprises a capacitor.

4. The sensor of claim 2 wherein the capacitor has a value which averages detected signals from hundreds to thousands of PRF pulses.

5. The sensor of claim 1 wherein the first and second impulse generators each comprise a driver and a pulse forming network connected to the driver.

6. The sensor of claim 1 wherein the fixed delay is equal to the round trip time to an object at a selected range.

7. The sensor of claim 1 wherein the PRF oscillator has a frequency of about 10 kHz to about 10 MHz.

8. The sensor of claim 1 wherein the fixed delay is a fraction of the PRF period.

9. The sensor of claim 8 wherein the fixed delay is about 10% of the PRF period.

10. The sensor of claim 1 wherein the fixed delay is about 4 ns to about 200 ns.

11. The sensor of claim 1 wherein the single transistor of the RF oscillator is a GaAsFET.

12. The sensor of claim 1 wherein the single diode detector comprises a Schottky diode having its anode connected to the pulsed RF oscillator and transmit/receive antenna, and a capacitor connected to its cathode.

13. The sensor of claim 1 further comprising a baseband amplifier connected to the single diode detector.

14. The sensor of claim 1 further comprising a threshold detector connected to the baseband amplifier.

15. A sensor for detecting the presence of a moving object at a selected range, comprising:

a PRF oscillator for producing a sequence of PRF pulses having a PRF period;

a first impulse generator connected to the PRF oscillator for generating a first impulse from each PRF pulse;

an adjustable range delay connected to the PRF oscillator and producing a fixed delay equal to the round trip time to the object at the selected range;

a second impulse generator connected to the adjustable range delay for generating a second impulse from each PRF pulse, the second impulse being delayed from the first impulse by the fixed delay;

a pulsed RF oscillator formed of a single transistor and connected to the first and second impulse generators for producing a pair of RF bursts from each PRF pulse, a first burst from the first impulse and a second burst from the second impulse, the second burst being delayed from the first burst by the fixed delay;

a single transmit/receive antenna connected to the pulsed RF oscillator for transmitting the first burst toward the object and receiving reflected pulses from the object;

a detector formed of a single diode having its anode connected to the pulsed RF oscillator and the transmit/receive antenna for mixing reflected pulses produced by the first burst with the second burst to produce a detected signal, and an averaging circuit for averaging a plurality of detected signals from a plurality of PRF pulses to produce an average DC detector signal;

a baseband amplifier connected to the single diode detector to amplify the average DC detector signal;

a threshold detector connected to the baseband amplifier to produce an output signal when the amplified average DC detector signal exceeds a threshold level.

16. The sensor of claim 15 wherein the fixed delay is a fraction of the PRF period.

17. The sensor of claim 16 wherein the fixed delay is about 10% of the PRF period.

18. The sensor of claim 15 wherein the fixed delay is about 4 ns to about 200 ns.

19. A method for detecting the presence of a moving object at a selected range, comprising:

producing a sequence of PRF pulses having a PRF period;

generating a first impulse from each PRF pulse;

generating a second impulse from each PRF pulse, the second impulse being delayed from the first impulse by a fixed delay corresponding to the selected range;

inputting the first and second impulses into a pulsed RF oscillator formed of a single transistor and producing a pair of RF bursts from each PRF pulse, a first burst from the first impulse and a second burst from the second impulse, the second burst being delayed from the first burst by the fixed delay;

transmitting the first burst from an antenna toward an object and receiving reflected pulses from the object at the same antenna;

mixing reflected pulses produced by the first burst with the second burst in a single diode detector to produce a detected signal, and averaging a plurality of detected signals from a plurality of PRF pulses to produce an average DC detector signal;

amplifying the average DC detector signal and producing an output signal when the amplified average DC detector signal exceeds a threshold level.

20. The method of claim 19 wherein the fixed delay is adjustably selected in the range of about 4 ns to about 200 ns.

* * * * *